US012742159B2

(12) United States Patent
Lee et al.

(10) Patent No.: US 12,742,159 B2
(45) Date of Patent: Sep. 22, 2026

(54) **L-GLUTAMIC ACID-PRODUCING MUTANT MICROORGANISM OF GENUS *CORYNEBACTERIUM*, AND METHOD FOR PRODUCING L-GLUTAMIC ACID USING SAME**

(71) Applicant: DAESANG CORPORATION, Seoul (KR)

(72) Inventors: Sun Hee Lee, Gyeonggi-do (KR); Hyun Ho Kim, Seoul (KR); Dong Hyun Kim, Seoul (KR); Hyun Sook Kim, Seoul (KR); Seok Hyun Park, Gyeonggi-do (KR); Joon Hyun Park, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 18/879,096

(22) PCT Filed: May 25, 2023

(86) PCT No.: PCT/KR2023/007159
§ 371 (c)(1),
(2) Date: Dec. 26, 2024

(87) PCT Pub. No.: WO2024/014696
PCT Pub. Date: Jan. 18, 2024

(65) Prior Publication Data

US 2026/0002135 A1 Jan. 1, 2026

(30) Foreign Application Priority Data

Jul. 11, 2022 (KR) ........................ 10-2022-0085236

(51) Int. Cl.
*C12N 9/04* (2006.01)
*C12N 1/20* (2006.01)
*C12N 15/77* (2006.01)
*C12P 13/14* (2006.01)
*C12R 1/15* (2006.01)

(52) U.S. Cl.
CPC ............. *C12N 9/0006* (2013.01); *C12N 1/20* (2013.01); *C12N 15/77* (2013.01); *C12P 13/14* (2013.01); *C12R 2001/15* (2021.05); *C12Y 101/0104* (2013.01)

(58) Field of Classification Search
CPC ............................... C12N 9/0006; C12P 13/14
See application file for complete search history.

(56) References Cited

U.S. PATENT DOCUMENTS

| | | | | |
|---|---|---|---|---|
| 6,852,516 | B2 | 2/2005 | Hibino et al. | |
| 6,962,805 | B2 | 11/2005 | Asakura et al. | |
| 2024/0076701 | A1 * | 3/2024 | Ma | C07K 14/34 |

FOREIGN PATENT DOCUMENTS

| | | | | |
|---|---|---|---|---|
| CN | 112725253 A * | 4/2021 | | C12Y 101/01037 |
| JP | 2014-36576 | 2/2014 | | |
| JP | 2017-506078 | 3/2017 | | |
| KR | 10-2207867 | 1/2021 | | |
| KR | 10-2269639 | 6/2021 | | |
| WO | 2022/143762 | 7/2022 | | |

OTHER PUBLICATIONS

English Translation of CN112725253. Retrieved on Jan. 29, 2026. (Year: 2026).*
International Search Report issued Sep. 5, 2023 in International (PCT) Application No. PCT/KR2023/007159.
NADP-dependent malic enzyme [Corynebaterium glutamicum), Protein, NCBI Reference Sequence: WP_216312831.1, Dec. 27, 2021.
Office Action issued Jan. 20, 2026 in corresponding Japanese Patent Application No. 2025-501658, with English translation, 6 pages.
Extended European Search Report dated May 4, 2026 in corresponding European Patent Application No. 23839790.5.
Gourdon et al., "Cloning of the Malic Enzyme Gene from *Corynebacterium glutamicum* and Role of the Enzyme in Lactate Metabolism.", Applied and Environmental Microbiology, vol. 66, No. 7, pp. 2981-2987 (Jul. 1, 2000).

* cited by examiner

*Primary Examiner* — Yong D Pak
(74) *Attorney, Agent, or Firm* — Wenderoth, Lind & Ponack, L.L.P.

(57) ABSTRACT

The present invention relates to a *Corynebacterium* sp. mutant microorganism producing L-glutamic acid and a method of producing L-glutamic acid using the same, and more specifically, to a novel NADP-dependent malic enzyme variant involved in the L-glutamic acid biosynthetic pathway, a polynucleotide, and a transformant, as well as a method of producing L-glutamic acid using the same. The NADP-dependent malic enzyme variant according to the present invention is obtained by substituting one or more amino acids in the amino acid sequence constituting NADP-dependent malic enzyme to change the enzymatic activity of the NADP-dependent malic enzyme, and a recombinant microorganism comprising the NADP-dependent malic enzyme variant is capable of efficiently producing L-glutamic acid.

1 Claim, 1 Drawing Sheet

Specification includes a Sequence Listing.

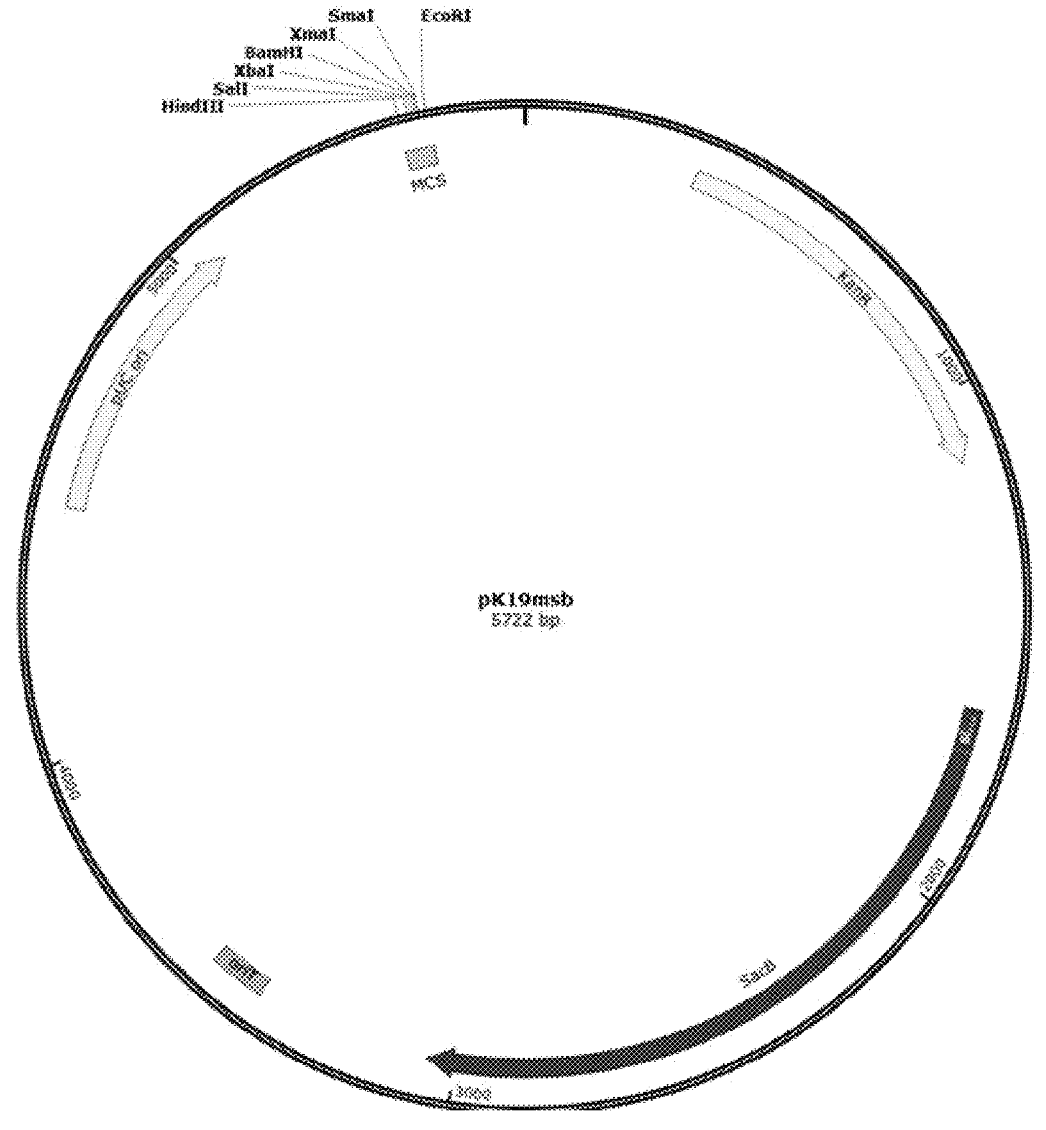
SmaI
EcoRI
XmaI
BamHI
XbaI
SalI
HindIII
MCS
pK19msb
5722 bp

SEQUENCE LISTING

```
Sequence total quantity: 9
SEQ ID NO: 1            moltype = DNA  length = 1179
FEATURE                 Location/Qualifiers
source                  1..1179
                        mol_type = other DNA
                        organism = synthetic construct
SEQUENCE: 1
atgaccatcg acctgcagcg ttccacccaa aacctcaccc atgaggaaat cttcgaggca  60
cacgagggcg gaaagctctc cattagttcc actcgtccgc tccgcgacat gcgcgatctt  120
tcccttgctt acaccccagg tgttgctcag gtttgtgaag caatcaaaga agatccagag  180
gttgcacgca cccacacggg cattggaaac accgtcgcgg ttatttccga cggcaccgct  240
```

```
gttcttggcc ttggcgatat cggacctcag gcatcccttc ccgtcatgga gggcaaggct  300
cagctgttca gctctttcgc tggtttgaag gctatcccta tcgttttgga tgttcacgat  360
gttgacgctt tggttgagac catcgcagcc atcgcgcctt ctttcggtgc tatcaacttg  420
gaggacatct ccgctcctcg ttgcttcgag gtggagcgcc gcctcatcga gcgtctcgat  480
attccagtta tgcacgatga ccagcacggc accgctgtgg ttatcctcgc tgcgctgcgc  540
aactccctga agctgctgga tcgcaagatc gaagacctca agattgttat ttccggcgca  600
ggcgcagcgg gcgttgcagc tgtagatatg ttgaccaatg ctggcgcaac cgacatcgtg  660
gttcttgatt cccgaggcat catccacgac agccgtgagg atctttcccc agttaaggct  720
gctctcgcgg agaagaccaa ccctcgtggc atcagcggtg gcatcaatga ggctttcacc  780
ggcgcggacc tgttcatcgg cgtgtccggc ggcaacatcg gcgaggacgc tctcaaactc  840
atggcaccac agccaatcct gttcaccctg gcgaacccaa ccccagagat cgatcctgaa  900
ctgtctcaga agtacggcgc catcgtcgcg accggccgct ctgacctgcc taaccagatc  960
aacaacgtgc tagcgttccc aggcattttc gccggcgctc tcgcagccaa ggccaagaag  1020
atcacccccg agatgaagct cgctgcagca gaggcaatcg ccgacatcgc agctgaggac  1080
ctcgaggtcg gccgcatcgt accgaccgcc ttgaatcccc gcgtcgcccc agcagtaaag  1140
gcagctgtcc aggccgtcgc cgaagcgcaa aacgcttag                        1179

SEQ ID NO: 2            moltype = AA  length = 392
FEATURE                 Location/Qualifiers
source                  1..392
                        mol_type = protein
                        organism = synthetic construct
SEQUENCE: 2
MTIDLQRSTQ NLTHEEIFEA HEGGKLSISS TRPLRDMRDL SLAYTPGVAQ VCEAIKEDPE  60
VARTHTGIGN TVAVISDGTA VLGLGDIGPQ ASLPVMEGKA QLFSSFAGLK AIPIVLDVHD  120
VDALVETIAA IAPSFGAINL EDISAPRCFE VERRLIERLD IPVMHDDQHG TAVVILAALR  180
NSLKLLDRKI EDLKIVISGA GAAGVAAVDM LTNAGATDIV VLDSRGIIHD SREDLSPVKA  240
ALAEKTNPRG ISGGINEAFT GADLFIGVSG GNIGEDALKL MAPQPILFTL ANPTPEIDPE  300
LSQKYGAIVA TGRSDLPNQI NNVLAFPGIF AGALAAKAKK ITPEMKLAAA EAIADIAAED  360
LEVGRIVPTA LNPRVAPAVK AAVQAVAEAQ NA                                392

SEQ ID NO: 3            moltype = DNA  length = 1179
FEATURE                 Location/Qualifiers
source                  1..1179
                        mol_type = genomic DNA
                        organism = Corynebacterium sp.
SEQUENCE: 3
atgaccatcg acctgcagcg ttccacccaa aacctcaccc atgaggaaat cttcgaggca  60
cacgagggcg gaaagctctc cattagttcc actcgtccgc tccgcgacat gcgcgatctt  120
tcccttgctt acaccccagg tgttgctcag gtttgtgaag caatcaaaga agatccagag  180
gttgcacgca cccacacggg cattggaaac accgtcgcgg ttatttccga cggcaccgct  240
gttcttggcc ttggcgatat cggacctcag gcatcccttc ccgtcatgga gggcaaggct  300
cagctgttca gctctttcgc tggtttgaag gctatcccta tcgttttgga tgttcacgat  360
gttgacgctt tggttgagac catcgcagcc atcgcgcctt ctttcggtgc tatcaacttg  420
gaggacatct ccgctcctcg ttgcttcgag gtggagcgcc gcctcatcga gcgtctcgat  480
attccagtta tgcacgatga ccagcacggc accgctgtgg ttatcctcgc tgcgctgcgc  540
aactccctga agctgctgga tcgcaagatc gaagacctca agattgttat ttccggcgca  600
ggcgcagcgg gcgttgcagc tgtagatatg ttgaccaatg ctggcgcaac cgacatcgtg  660
gttcttgatt cccgaggcat catccacgac agccgtgagg atctttcccc agttaaggct  720
gctctcgcgg agaagaccaa ccctcgtggc atcagcggtg gcatcaatga ggctttcacc  780
ggcgcggacc tgttcatcgg cgtgtccggc ggcaacatcg gcgaggacgc tctcaaactc  840
atggcaccac agccaatcct gttcaccctg gcgaacccaa ccccagagat cgatcctgaa  900
ctgtctcaga agtacggcgc catcgtcgcg accggccgct ctgacctgcc taaccagatc  960
aacaacgtgc tagcgttccc aggcattttc gccggcgctc tcgcagccaa ggccaagaag  1020
atcacccccg agatgaagct cgctgcagca gaggcaatcg ccgacatcgc agctgaggac  1080
ctcgaggtcg gccgcatcgt accgaccgcc ttggatcccc gcgtcgcccc agcagtaaag  1140
gcagctgtcc aggccgtcgc cgaagcgcaa aacgcttag                        1179

SEQ ID NO: 4            moltype = AA  length = 392
FEATURE                 Location/Qualifiers
source                  1..392
                        mol_type = protein
                        organism = Corynebacterium sp.
SEQUENCE: 4
MTIDLQRSTQ NLTHEEIFEA HEGGKLSISS TRPLRDMRDL SLAYTPGVAQ VCEAIKEDPE  60
VARTHTGIGN TVAVISDGTA VLGLGDIGPQ ASLPVMEGKA QLFSSFAGLK AIPIVLDVHD  120
VDALVETIAA IAPSFGAINL EDISAPRCFE VERRLIERLD IPVMHDDQHG TAVVILAALR  180
NSLKLLDRKI EDLKIVISGA GAAGVAAVDM LTNAGATDIV VLDSRGIIHD SREDLSPVKA  240
ALAEKTNPRG ISGGINEAFT GADLFIGVSG GNIGEDALKL MAPQPILFTL ANPTPEIDPE  300
LSQKYGAIVA TGRSDLPNQI NNVLAFPGIF AGALAAKAKK ITPEMKLAAA EAIADIAAED  360
LEVGRIVPTA LDPRVAPAVK AAVQAVAEAQ NA                                392

SEQ ID NO: 5            moltype = DNA  length = 5719
FEATURE                 Location/Qualifiers
source                  1..5719
                        mol_type = other DNA
                        organism = synthetic construct
SEQUENCE: 5
tgccgcaagc actcagggcg caagggctgc taaaggaagc ggaacacgta gaaagccagt  60
```

-continued

```
ccgcagaaac ggtgctgacc ccggatgaat gtcagctact gggctatctg gacaagggaa  120
aacgcaagcg caaagagaaa gcaggtagct tgcagtgggc ttacatggcg atagctagac  180
tgggcggttt tatggacagc aagcgaaccg gaattgccag ctggggcgcc ctctggtaag  240
gttgggaagc cctgcaaagt aaactggatg gctttcttgc cgccaaggat ctgatggcgc  300
aggggatcaa gatctgatca agagacagga tgaggatcgt ttcgcatgat tgaacaagat  360
ggattgcacg caggttctcc ggccgcttgg gtggagaggc tattcggcta tgactgggca  420
caacagacaa tcggctgctc tgatgccgcc gtgttccggc tgtcagcgca ggggcgcccg  480
gttctttttg tcaagaccga cctgtccggt gccctgaatg aactccaaga cgaggcagcg  540
cggctatcgt ggctggccac gacgggcgtt ccttgcgcag ctgtgctcga cgttgtcact  600
gaagcgggaa gggactggct gctattgggc gaagtgccgg ggcaggatct cctgtcatct  660
caccttgctc ctgccgagaa agtatccatc atggctgatg caatgcggcg gctgcatacg  720
cttgatccgg ctacctgccc attcgaccac caagcgaaac atcgcatcga gcgagcacgt  780
actcggatgg aagccggtct tgtcgatcag gatgatctgg acgaagagca tcaggggctc  840
gcgccagccg aactgttcgc caggctcaag gcgcggatgc ccgacggcga ggatctcgtc  900
gtgacccatg gcgatgcctg cttgccgaat atcatggtgg aaaatggccg cttttctgga  960
ttcatcgact gtggccggct gggtgtggcg gaccgctatc aggacatagc gttggctacc  1020
cgtgatattg ctgaagagct tggcggcgaa tgggctgacc gcttcctcgt gctttacggt  1080
atcgccgctc ccgattcgca gcgcatcgcc ttctatcgcc ttcttgacga gttcttctga  1140
gcgggactct ggggttcgct agaggatcga tcctttttaa cccatcacat atacctgccg  1200
ttcactatta tttagtgaaa tgagatatta tgatattttc tgaattgtga ttaaaaaggc  1260
aactttatgc ccatgcaaca gaaactataa aaaatacaga gaatgaaaag aaacagatag  1320
atttttagt tctttaggcc cgtagtctgc aaatcctttt atgattttct atcaaacaaa  1380
agaggaaaat agaccagttg caatccaaac gagagtctaa tagaatgagg tcgaaaagta  1440
aatcgcgcgg gtttgttact gataaagcag gcaagaccta aaatgtgtaa agggcaaagt  1500
gtatactttg gcgtcacccc ttacatattt taggtctttt tttattgtgc gtaactaact  1560
tgccatcttc aaacaggagg gctggaagaa gcagaccgct aacacagtac ataaaaaagg  1620
agacatgaac gatgaacatc aaaaagtttg caaaacaagc aacagtatta acctttacta  1680
ccgcactgct ggcaggaggc gcaactcaag cgtttgcgaa agaaacgaac caaaagccat  1740
ataaggaaac atacggcatt tcccatatta cacgccatga tatgctgcaa atccctgaac  1800
agcaaaaaaa tgaaaaatat caagtttctg aatttgattc gtccacaatt aaaaatatct  1860
cttctgcaaa aggcctggac gtttgggaca gctggccatt acaaaacgct gacggcactg  1920
tcgcaaacta tcacggctac cacatcgtct ttgcattagc cggagatcct aaaaatgcgg  1980
atgacacatc gatttacatg ttctatcaaa aagtcggcga aacttctatt gacagctgga  2040
aaaacgctgg ccgcgtcttt aaagacagcg acaaattcga tgcaaatgat tctatcctaa  2100
aagaccaaac acaagaatgg tcaggttcag ccacatttac atctgacgga aaaatccgtt  2160
tattctacac tgatttctcc ggtaaacatt acggcaaaca aacactgaca actgcacaag  2220
ttaacgtatc agcatcagac agctctttga acatcaacgg tgtagaggat tataaatcaa  2280
tctttgacgg tgacggaaaa acgtatcaaa atgtacagca gttcatcgat gaaggcaact  2340
acagctcagg cgacaaccat acgctgagag atcctcacta cgtagaagat aaaggccaca  2400
aatacttagt atttgaagca aacactggaa ctgaagatgg ctaccaaggc gaagaatctt  2460
tatttaacaa agcatactat ggcaaaagca catcattctt ccgtcaagaa agtcaaaaac  2520
ttctgcaaag cgataaaaaa cgcacggctg agttagcaaa cggcgctctc ggtatgattg  2580
agctaaacga tgattacaca ctgaaaaaag tgatgaaacc gctgattgca tctaacacag  2640
taacagatga aattgaacgc gcgaacgtct ttaaaatgaa cggcaaatgg tacctgttca  2700
ctgactcccg cggatcaaaa atgacgattg acggcattac gtctaacgat atttacatgc  2760
ttggttatgt ttctaattct ttaactggcc catacaagcc gctgaacaaa actggccttg  2820
tgttaaaaat ggatcttgat cctaacgatg taacctttac ttactcacac ttcgctgtac  2880
ctcaagcgaa aggaaacaat gtcgtgatta caagctatat gacaaacaga ggattctacg  2940
cagacaaaca atcaacgttt gcgccgagct tcctgctgaa catcaaaggc aagaaaacat  3000
ctgttgtcaa agacagcatc cttgaacaag gacaattaac agttaacaaa taaaaacgca  3060
aaagaaaatg ccgatgggta ccgagcgaaa tgaccgacca agcgacgccc aacctgccat  3120
cacgagattt cgattccacc gccgccttct atgaaaggtt gggcttcgga atcgttttcc  3180
gggacgccct cgcggacgtg ctcatagtcc acgacgcccg tgattttgta gccctggccg  3240
acggccagca ggtaggccga caggctcatg ccggccgccg ccgccttttc ctcaatcgct  3300
cttcgttcgt ctggaaggca gtacaccttg ataggtgggc tgcccttcct ggttggcttg  3360
gtttcatcag ccatccgctt gccctcatct gttacgccgg cggtagccgg ccagcctcgc  3420
agagcaggat tcccgttgag caccgccagg tgcgaataag ggacagtgaa gaaggaacac  3480
ccgctcgcgg gtgggcctac ttcacctatc ctgcccggct gacgccgttg gatacaccaa  3540
ggaaagtcta cacgaaccct ttggcaaaat cctgtatatc gtgcgaaaaa ggatggatat  3600
accgaaaaaa tcgctataat gaccccgaag cagggttatg cagcggaaaa gcgctgcttc  3660
cctgctgttt tgtggaatat ctaccgactg gaaacaggca aatgcaggaa attactgaac  3720
tgaggggaca ggcgagagac gatgccaaag agctcctgaa aatctcgata actcaaaaaa  3780
tacgcccggt agtgatctta tttcattatg gtgaaagttg gaacctctta cgtgccgatc  3840
aacgtctcat tttcgccaaa agttggccca gggcttcccg gtatcaacag ggacaccagg  3900
atttatttat tctgcgaagt gatcttccgt cacaggtatt tattcggcgc aaagtgcgtc  3960
gggtgatgct gccaacttac tgatttagtg tatgatggtg tttttgaggt gctccagtgg  4020
cttctgtttc tatcagctcc tgaaaatctc gataactcaa aaaatacgcc cggtagtgat  4080
cttatttcat tatggtgaaa gttggaacct cttacgtgcc gatcaacgtc tcattttcgc  4140
caaaagttgg cccagggctt cccggtatca acagggacac caggatttat ttattctgcg  4200
aagtgatctt ccgtcacagg tatttattcg gcgcaaagtg cgtcgggtga tgctgccaac  4260
ttactgattt agtgtatgat ggtgtttttg aggtgctcca gtggcttctg tttctatcag  4320
ggctggatga tcctccagcg cggggatctc atgctggagt tcttcgccca ccccaaaagg  4380
atctaggtga agatcctttt tgataatctc atgaccaaaa tcccttaacg tgagttttcg  4440
ttccactgag cgtcagaccc cgtagaaaag atcaaaggat cttcttgaga tccttttttt  4500
ctgcgcgtaa tctgctgctt gcaaacaaaa aaaccaccgc taccagcggt ggtttgtttg  4560
ccggatcaag agctaccaac tctttttccg aaggtaactg gcttcagcag agcgcagata  4620
ccaaatactg ttcttctagt gtagccgtag ttaggccacc acttcaagaa ctctgtagca  4680
ccgcctacat acctcgctct gctaatcctg ttaccagtgg ctgctgccag tggcgataag  4740
tcgtgtctta ccgggttgga ctcaagacga tagttaccgg ataaggcgca gcggtcgggc  4800
```

-continued

```
tgaacggggg gttcgtgcac acagcccagc ttggagcgaa cgacctacac cgaactgaga  4860
tacctacagc gtgagctatg agaaagcgcc acgcttcccg aagggagaaa ggcggacagg  4920
tatccggtaa gcggcagggt cggaacagga gagcgcacga gggagcttcc agggggaaac  4980
gcctggtatc tttatagtcc tgtcgggttt cgccacctct gacttgagcg tcgatttttg  5040
tgatgctcgt caggggggcg gagcctatgg aaaaacgcca gcaacgcggc ctttttacgg  5100
ttcctggcct tttgctggcc ttttgctcac atgttctttc ctgcgttatc ccctgattct  5160
gtggataacc gtattaccgc ctttgagtga gctgataccg ctcgccgcag ccgaacgacc  5220
gagcgcagcg agtcagtgag cgaggaagcg gaagagcgcc caatacgcaa accgcctctc  5280
cccgcgcgtt ggccgattca ttaatgcagc tggcacgaca ggtttcccga ctggaaagcg  5340
ggcagtgagc gcaacgcaat taatgtgagt tagctcactc attaggcacc ccaggcttta  5400
cactttatgc ttccggctcg tatgttgtgt ggaattgtga gcggataaca atttcacaca  5460
ggaaacagct atgacatgat tacgccaagc ttgcatgcct gcaggtcgac tctagaggat  5520
ccccgggtac cgagctcgaa ttcactggcc gtcgttttac aacgtcgtga ctgggaaaac  5580
cctggcgtta cccaacttaa tcgccttgca gcacatcccc ctttcgccag ctggcgtaat  5640
agcgaagagg cccgcaccga tcgcccttcc caacagttgc gcagcctgaa tggcgaatgg  5700
cgataagcta gcttcacgc                                                5719

SEQ ID NO: 6            moltype = DNA  length = 23
FEATURE                 Location/Qualifiers
source                  1..23
                        mol_type = other DNA
                        organism = synthetic construct
SEQUENCE: 6
catcgagcgt ctcgatattc cag                                           23

SEQ ID NO: 7            moltype = DNA  length = 20
FEATURE                 Location/Qualifiers
source                  1..20
                        mol_type = other DNA
                        organism = synthetic construct
SEQUENCE: 7
cgcggggatt caaggcggtc                                               20

SEQ ID NO: 8            moltype = DNA  length = 19
FEATURE                 Location/Qualifiers
source                  1..19
                        mol_type = other DNA
                        organism = synthetic construct
SEQUENCE: 8
gaccgccttg aatccccgc                                                19

SEQ ID NO: 9            moltype = DNA  length = 23
FEATURE                 Location/Qualifiers
source                  1..23
                        mol_type = other DNA
                        organism = synthetic construct
SEQUENCE: 9
aacttctatg acctgcgtag cat                                           23
```

L-GLUTAMIC ACID-PRODUCING MUTANT MICROORGANISM OF GENUS *CORYNEBACTERIUM*, AND METHOD FOR PRODUCING L-GLUTAMIC ACID USING SAME

SEQUENCE LISTING

A sequence listing in electronic (XML file) format is filed with this application and incorporated herein by reference. The name of the XML file is "Sequence_Listing-1879A.xml"; the file was created on Dec. 23, 2024; the size of the file is 17,614 bytes.

TECHNICAL FIELD

The present invention relates to a *Corynebacterium* sp. mutant microorganism producing L-glutamic acid and a method of producing L-glutamic acid using the same, and more specifically, to a novel NADP-dependent malic enzyme variant involved in the L-glutamic acid biosynthetic pathway, a polynucleotide, and a transformant, as well as a method of producing L-glutamic acid using the same.

BACKGROUND ART

L-glutamic acid is a typical amino acid that is produced by microbial fermentation. Monosodium L-glutamate (MSG) may increase the preference of foods such as meat, fish, chicken, vegetables, sauces, soups and seasonings by balancing and harmonizing the overall taste of the food, may enhance the taste of low-salt foods having a salt content reduced up to 30%, and thus is widely used as a household seasoning and a seasoning for the production of processed food.

In brief, regarding the pathway of L-glutamic acid fermentation, glucose mainly undergoes the glycolytic pathway (EMP), but a portion thereof is metabolized into two pyruvic acid molecules through the pentose phosphate pathway. Among these molecules, one molecule combines with $CO_2$ to form oxaloacetic acid, and the other molecule combines with acetyl CoA from pyruvic acid to form citric acid. Then, oxaloacetic acid and citric acid enter the citric acid cycle (TCA cycle) to form α-ketoglutaric acid. Here, since the TCA cycle lacks the metabolic pathway for the oxidation of α-ketoglutaric acid to succinic acid and isocitrate dehydrogenase and glutamate dehydrogenase are closely involved therein, reductive amination of α-ketoglutaric acid efficiently occurs, thus producing L-glutamic acid.

For the production of L-glutamic acid, either naturally occurring wild-type strains or mutant strains modified from the wild-type strains so as to have an increased ability to produce glutamic acid may be used. In recent years, n order to improve the efficiency of production of L-glutamic acid, there has been development of a variety of recombinant strains or mutant strains having excellent L-glutamic acid productivity by applying genetic recombination technology to microorganisms such as *Escherichia coli* and *Corynebacterium*, which are widely used in the production of useful substances such as amino acids and nucleic acids, and methods of producing L-glutamic acid using the same. In particular, there have been attempts to increase the production of L-glutamic acid by targeting genes such as enzymes, transcription factors and transport proteins, which are involved in the biosynthetic pathways of L-glutamic acid, or by inducing mutations in promoters that regulate the expression of these genes. However, there are dozens of types of proteins such as enzymes, transcription factors and transport proteins, which are involved directly or indirectly in the production of L-glutamic acid, and thus much research is still needed on the increase in L-glutamic acid productivity by changes in the activity of these proteins.

PRIOR ART DOCUMENTS

Patent Documents

U.S. Pat. No. 6,852,516
U.S. Pat. No. 6,962,805

DISCLOSURE

Technical Problem

An object of the present invention is to provide a novel NADP-dependent malic enzyme variant.

Another object of the present invention is to provide a polynucleotide encoding the variant.

Still another object of the present invention is to provide a transformant comprising the variant or polynucleotide.

Yet another object of the present invention is to provide a method of producing L-glutamic acid using the transformant.

Technical Solution

One aspect of the present invention provides an NADP-dependent malic enzyme variant consisting of the amino acid sequence of SEQ ID NO: 2 in which aspartic acid at position 372 in the amino acid sequence of SEQ ID NO: 4 is substituted with asparagine.

As used in the present invention, the term "NADP-dependent malic enzyme" is an enzyme that catalyzes the oxidative decarboxylation of malic acid to pyruvate and $CO_2$ and produces NADPH, and it serves to supply a carbon source necessary for the citric acid cycle. The NADP-dependent malic enzyme may be a gene encoding NADP-dependent malic enzyme or a sequence having substantial identity thereto. As used herein, the term "substantial identity" means that, when each gene sequence, i.e., a base sequence nucleotide sequence, and any other nucleotide sequence are aligned to correspond to each other as much as possible and analyzed, the other nucleotide sequence has a sequence homology of at least 70%, at least 80%, at least 90%, or at least 98% with each nucleotide sequence.

The NADP-dependent malic enzyme in the present invention comprises the amino acid sequence of SEQ ID NO: 4.

According to one embodiment of the present invention, the amino acid sequence of SEQ ID NO: 4 may be derived from a wild-type *Corynebacterium* sp. microorganism.

More specifically, the *Corynebacterium* sp, microorganism may be *Corynebacterium glutamicum*.

As used in the present invention, the term "variant" refers to a polypeptide which is obtained by conservative substitution, deletion, modification or addition of one or more amino acids at the N-terminus, C-terminus of and/or within the amino acid sequence of a specific protein and has an amino acid sequence different from that of the protein before mutation, but retains functions properties of the protein before mutation. As used herein, the "conservative substitution" means substituting one amino acid with another amino acid having similar structural and/or chemical properties. The conservative substitution may have little or no impact on the activity of the protein or polypeptide. The amino acid is selected from among alanine (Ala), isoleucine (Ile), valine (Val), leucine (Leu), methionine (Met), asparagine (Asn), cysteine (Cys), glutamine (Gln), serine (Ser), threonine (Thr), phenylalanine (Phe); tryptophan (Trp), tyrosine (Tyr), aspartic acid (Asp), glutamic acid (Glu), arginine (Arg), histidine (His), lysine (Lys), glycine (Gly), and proline (Pro).

In addition, some variants include those in which one or more portions, such as an N-terminal leader sequence or transmembrane domain, have been removed, or those in which a portion has been removed from the N- and/or C-terminus of a mature protein.

The variant may have increased (enhanced), unchanged, or decreased (weakened) ability compared to that of the protein or polypeptide before mutation. Here, the term "increased or enhanced" includes: a case in which the activity of the protein itself has increased compared to the activity of the protein before mutation; a case in which the overall activity of the protein in the cell is higher than that in the wild-type strain or the strain expressing the protein before mutation due to increased expression or translation of the gene encoding the protein; and a combination thereof. In addition, the term "decreased or weakened" includes: a case in which the activity of the protein itself has decreased compared to the activity of the protein before mutation; a case in which the overall activity of the protein in the cell is lower than that in the wild-type strain or the strain expressing the protein before mutation due to reduced expression or translation of the gene encoding the protein; and a combination thereof. In the present invention, the term "variant" may be used interchangeably with terms such as variant type, modification, variant polypeptide, mutated protein, mutation, and the like.

The variant in the present invention may be an NADP-dependent malic enzyme variant consisting of the amino acid sequence of SEQ ID NO: 2 in which the amino acid aspartic acid at position 372 in the amino acid sequence of SEQ ID NO: 4 is substituted with asparagine.

Another aspect of the present invention provides a polynucleotide encoding the NADP-dependent malic enzyme variant.

As used in the present invention, the term "polynucleotide" refers to a DNA or RNA strand having a certain length or more, which is a long-chain polymer of nucleotides formed by linking nucleotide monomers via covalent bonds. More specifically, the term "polynucleotide" refers to a polynucleotide fragment encoding the variant.

The polynucleotide may comprise a nucleotide sequence encoding the amino acid sequence of SEQ ID NO: 2.

According to one embodiment of the present invention, the polynucleotide may comprise the nucleotide sequence represented by SEQ ID NO: 1.

Still another aspect of the present invention provides a vector comprising a polynucleotide encoding the NADP-dependent malic enzyme variant.

Yet another aspect of the present invention provides a transformant comprising the NADP-dependent malic enzyme variant or the polynucleotide.

As used in the present invention, the term "vector" refers to any type of nucleic acid sequence transfer structure that is used as a means for transferring and expressing a gene of interest in a host cell. Unless otherwise specified, the term "vector" may mean one allowing the nucleic acid sequence contained therein to be expressed after insertion into the host cell genome and/or one allowing the nucleic acid sequence to be expressed independently. This vector comprises essential regulatory elements operably linked so that an inserted gene can be expressed. As used herein, the term "operably linked" means that a gene of interest and regulatory sequences thereof are functionally linked together in a manner enabling gene expression, and the "regulatory elements" include a promoter for initiating transcription, any operator sequence for regulating transcription, a sequence encoding suitable mRNA ribosome-binding sites, and a sequence for regulating termination of transcription and translation.

The vector in the present invention is not particularly limited as long as it may replicate in a host cell, and any vector known in the art may be used, Examples of the vector include a natural or recombinant plasmid, cosmid, virus and bacteriophage. Examples of a phage vector or cosmid vector include, but are not limited to, pWE15, M13, λMBL3, λMBL4, λIXII, λASHII, λAPII, λt10, λt11, Charon4A, and Charon21A, and examples of a plasmid vector include, but are not limited to, pBR series, pUC series, pBluescriptII series, pGEM series, pTZ series, pCL series, and pET series.

The vector may typically be constructed as a vector for cloning or as a vector for expression. The vector for expression may be a conventional vector that is used in the art to express a foreign gene or protein in a plant, animal, or microorganism, and may be constructed through various methods known in the art.

As used in the present invention, the term "recombinant vector" may be transformed into a suitable host cell, and then may replicate regardless of the genome of the host cell or may be integrated into the genome itself. In this case, the "suitable host cell" may contain a replication origin, which is a particular nucleotide sequence which enables the vector to replicate in the suitable host cell and from which replication starts. For example, when the vector used is an expression vector and uses a prokaryotic cell as a host, the vector generally comprises a strong promoter capable of promoting transcription (e.g., pLλ promoter, CMV promoter, trp promoter, lac promoter, tac promoter, T7 promoter, etc.), a ribosome binding site for initiation of translation, and a transcription/translation termination sequence. When a eukaryotic cell is used as a host, the vector comprises a replication origin operating in the eukaryotic cell, and examples of the replication origin include, but are not limited to, an f1 replication origin, an SV40 replication origin, a pMB1 replication origin, an adeno replication origin, an AAV replication origin, and a BBV replication origin. In addition, the recombinant vector may comprise a promoter derived from the genome of a mammalian cell (e.g., metallothionein promoter) or a promoter derived from a mammalian virus (e.g., adenovirus late promoter, vaccinia virus 7.5K promoter, SV40 promoter, cytomegalovirus promoter, HSV-tk promoter, etc.), and generally has a polyadenylation sequence as a transcription termination sequence.

The recombinant vector may comprise a selection marker. The selection marker Serves to select a transformant (host cell) transformed with the vector, and since only cells expressing the selection marker can survive in the medium treated with the selection marker, it is possible to select transformed cells. Representative examples of the selection marker include, but are not limited to, kanamycin, streptomycin, and chloramphenicol.

The transformant may be produced by inserting the recombinant vector into a host cell, and the transformant may be obtained by introducing the recombinant vector into an appropriate host cell. The host cell is a cell capable of stably and continuously cloning or expressing the expression vector, and any host cell known in the art may be used.

Where the vector is transformed into prokaryotic cells to generate recombinant microorganisms, examples of host cells that may be used include, but are not limited to, *E. coli* sp. strains such as *E. coli* JM109, *E. coli* BL21, *E. coli* RR1, *E. coli* LE392, *E. coli* B, *E. coli* X 1776, *E. coli* W3110, and *E. coli* XL1-Blue, *Bacillus* sp. strains such as *Bacillus subtilis* and *Bacillus thuringiensis, Corynebacterium* sp. strains, and various Enterobacteriaceae strains such as *Salmonella typhimurium, Serratia marcescens*, and *Pseudomonas* species.

Where the vector is transformed into eukaryotic cells to generate recombinant microorganisms, examples of host cells that may be used include, but are not limited to, yeast (e.g., *Saccharomyces cerevisiae*), insect cells, plant cells and animal cells, such as Sp2/0, CHO K1, CHO DG44, PER.C6, W138, BHK, COS7, 293, HepG2, Huh7, 3T3, RIN, and MDCK cell lines.

As used in the present invention, the term "transformation" refers to a phenomenon in which external DNA is introduced into a host cell, thereby artificially causing genetic changes, and the term "transformant" refers to a host cell into which external DNA has been introduced and in which the expression of the gene of interest is stably maintained.

The transformation may be performed using a suitable vector introduction technique selected depending on the host cell, so that the gene of interest or a recombinant vector comprising the same may be expressed in the host cell. For example, introduction of the vector may be performed by electroporation, heat-shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or any combination thereof, without being limited thereto. As long as the transformed gene may be expressed in the host cell, it may be inserted into the chromosome of the host cell, or may exist extrachromosomally, without being limited thereto.

The transformant may include a cell transfected, transformed, or infected with the recombinant vector of the present invention in vivo or in vitro, and may be used in the same sense as a recombinant host cell, a recombinant cell, or a recombinant microorganism.

According to one embodiment of the present invention, the transformant may be a *Corynebacterium* sp. microorganism.

More specifically, examples of the *Corynebacterium* sp. microorganism include, but are not limited to, *Corynebacterium glutamicum, Corynebacterium crudilactis, Corynebacterium deserti, Corynebacterium callunae, Corynebacterium suranareeae, Corynebacterium lubricantis, Corynebacterium doosanense, Corynebacterium efficiens, Corynebacterium uterequi, Corynebacterium stationis, Corynebacterium pacaense, Corynebacterium singulare, Corynebacterium humireducens, Corynebacterium marinum, Corynebacterium halotolerans, Corynebacterium spheniscorum, Corynebacterium freiburgense, Corynebacterium striatum, Corynebacterium canis, Corynebacterium ammoniagenes, Corynebacterium renale, Corynebacterium pollutisoli, Corynebacterium imitans, Corynebacterium caspium, Corynebacterium testudinoris, Corynebacterium pseudopelargi*, and *Corynebacterium flavescens.*

The transformant in the present invention may be a strain either comprising the above-described NADP-dependent malic enzyme variant or a polynucleotide encoding the same or comprising the vector comprising the same, a strain expressing the NADP-dependent malic enzyme variant or the polynucleotide, or a strain having activity for the NADP-dependent malic enzyme variant, without being limited thereto.

According to one embodiment of the present invention, the transformant may have the ability to produce L-glutamic acid.

The transformant may naturally have the ability to produce L-glutamic acid or may be one artificially endowed with the ability to produce L-glutamic acid.

According to one embodiment of the present invention, the transformant may have an increased ability to produce L-glutamic acid, due to a change in the activity of NADP-dependent malic enzyme.

As used in the present invention, the term "increased ability to produce" means that L-glutamic acid productivity has increased compared to that of the parent strain. As used herein, the term "parent strain" refers to a wild-type strain or mutant strain to be mutated, and includes a strain that is to be mutated directly or to be transformed with a recombinant vector or the like. In the present invention, the parent strain may be a wild-type *Corynebacterium* sp. microorganism or a *Corynebacterium* sp. microorganism mutated from the wild-type microorganism.

The transformant according to the present invention exhibits an increased ability to produce L-glutamic acid compared to the parent strain, due to the change in the activity of NADP-dependent malic enzyme caused by introduction of the NADP-dependent malic enzyme variant thereinto. More specifically, the amount of L-glutamic acid produced by the transformant may be at least 18, 58, 10%, 15%, 20%, 25%, 30%, 358, 40%, 45%, 508, 558, 60%, 65%, 70%, 75%, 80%, 85%, 908, 95%, or 100% higher than that produced by the parent strain, or may be 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold higher than that produced by the parent strain, without being limited thereto. For example, the amount of L-glutamic acid produced by the transformant comprising the NADP-dependent malic enzyme variant may be at least 5%, specifically 5 to 50% (preferably 7 to 30%) higher than that produced by the parent strain.

Still yet another aspect of the present invention provides a method for producing L-glutamic acid, comprising steps of: culturing the transformant in a medium; and recovering L-glutamic acid from the transformant or the medium in which the transformant has been cultured.

The culturing may be performed using a suitable medium and culture conditions known in the art, and any person skilled in the art may easily adjust and use the medium and the culture conditions. Specifically, the medium may be a liquid medium, without being limited thereto.

Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For culture media for *Corynebacterium* sp. microorganisms, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, without being limited thereto. Examples of nitrogen sources that may be used include peptone, yeast extract, meat extract, malt extract, meal, corn steep liquor, soybean urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present invention, in the step of recovering L-glutamic acid from the cultured transformant or the medium in which the transformant has been cultured, the produced L-glutamic acid may be collected or recovered from the medium using a suitable method known in the art depending on the culture method. Examples of a method that may be used to recover the produced L-glutamic acid include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present invention, the step of recovering L-glutamic acid may be performed by centrifuging the culture medium at a low speed to remove biomass and separating the obtained supernatant through ion-exchange chromatography.

According to one embodiment of the present invention, the step of recovering L-glutamic acid may include a process of purifying the L-glutamic acid.

Advantageous Effects

The NADP-dependent malic enzyme variant according to the present invention is obtained by substituting one or more amino acids in the amino acid sequence constituting NADP-dependent malic enzyme to change the enzymatic activity of the NADP-dependent malic enzyme, and a recombinant microorganism comprising the NADP-dependent malic enzyme variant is capable of efficiently producing L-glutamic acid.

BRIEF DESCRIPTION OF DRAWINGS

FIG. 1 shows the structure of plasmid pk19msb according to one embodiment of the present invention.

MODE FOR INVENTION

Hereinafter, the present invention will be described in more detail. However, this description is merely presented by way of example to facilitate the understanding of the present invention, and the scope of the present invention is not limited by this exemplary description.

Example 1. Construction of Vector for Expression of NADP-Dependent Malic Enzyme Variant A vector for expression of a variant having a substitution of asparagine (N) for aspartic acid (D) at position 372 in the amino acid sequence of NADP-dependent malic enzyme (SEQ ID NO: 4) was constructed.

Using the gDNA of wild-type *Corynebacterium glutamicum* ATCC13869 as a template, PCR reactions were performed using a primer pair of primer 1 and primer 2 and a primer pair of primer 3 and primer 4, respectively. Thereafter, using a mixture of the two PCR products as a template, overlapping PCR was performed using primer 1 and primer 4 to obtain a fragment. Here, Takara PrimeSTAR Max DNA polymerase was used as polymerase, and PCR amplification was performed under the following conditions: denaturation at 95° C. for 5 min, and then 30 cycles, each consisting of 95° C. for 30 sec, 58° C. for 30 sec, and 72° C. for 1 min and 30 sec, followed by reaction at 72° C. for 5 min. A pK19msb vector was treated with smaI and ligated with the PCR product (fragment) obtained above, and the resulting plasmid was named pK_malE (D372N).

The primer sequences used for vector construction are as shown in Table 1 below.

TABLE 1

| Primer name | SEQ ID NO. | Primer sequence (5'→3') |
|---|---|---|
| Primer 1 | 6 | CATCGAGCGTCTCGATATTCCAG |
| Primer 2 | 7 | CGCGGGGATTCAAGGCGGTC |
| Primer 3 | 8 | GACCGCCTTGAATCCCCGC |
| Primer 4 | 9 | AACTTCTATGACCTGCGTAGCAT |

Example 2. Construction of Mutant Strain into which NADP-Dependent Malic Enzyme Variant has been Introduced

*Corynebacterium glutamicum* 03 (KCCM13218P) was used as a parent strain into which the NADP-dependent malic enzyme variant was to be introduced, and an electro-competent cell preparation method, a modification of the method of van der Rest et al., was used as a method for transformation of the U3 strain.

First, the U3 strain was primarily cultured in 10 mL of 2YT medium (containing 16 g/l of tryptone, 10 g/l of yeast extract, and 5 g/l of sodium chloride) supplemented with 2% glucose, thus preparing a seed culture. Thereafter, isonicotinic acid hydrazine at a concentration of 1 mg/ml and 2.5% glycine were added to 100 ml of 2YT medium free of glucose, and the seed culture was inoculated into the 2YT medium to reach an $OD_{610}$ value of 0.3, and then cultured at 18° C. and 180 rpm for 12 to 16 hours so that the $OD_{610}$ value reached 1.2 to 1.4. The culture was kept on ice for 30 minutes, and then centrifuged at 4,000 rpm at 4° C. for 15 minutes. Thereafter, the supernatant was discarded and the precipitated U3 strain was washed 4 times with a 10% glycerol solution and finally re-suspended in 0.5 ml of a 10% glycerol solution, thereby preparing competent cells. Electroporation was performed using a Bio-Rad electroporator. The prepared competent cells and the constructed pK_malE (D372N) vector were placed in an electroporation cuvette (0.2 mm), and then subjected to electroporation under conditions of 2.5 kV, 200Ω and 12.5 μF. Immediately after completion of the electroporation, 1 ml of a regeneration medium (containing 18.5 g/l brain heart infusion and 0.5 M sorbitol) was added to the cells which were then heat-treated at 46° C. for 6 minutes. Next, the cells were cooled at room temperature, transferred into a 15-ml cap tube, incubated at 30° C. for 2 hours, and plated on a selection medium (containing 5 g/l tryptone, 5 g/l NaCl, 2.5 g/l yeast extract, 18.5 g/l brain heart infusion powder, 15 g/l agar, 91 g/l sorbitol, and 20 μg/1 kanamycin). The cells were cultured at 30° C. for 72 hours, and the generated colonies were cultured in BHI medium until the stationary phase to induce secondary recombination. Then, the cells were diluted to 10-5 to 10-7, and plated on an antibiotic-free 2YT plate medium (containing 10% sucrose), and a strain having no kanamycin resistance and grown on the medium containing 10% sucrose was selected and named NMD1.

Experimental Example 1. Evaluation of L-Glutamic Acid Productivity of Mutant Strain into which NADP-Dependent Malic Enzyme Variant has been Introduced L-glutamic acid productivity was compared between the parent strain 03 and the mutant strain NMD1 into which the NADP-dependent malic enzyme variant has been introduced.

Each strain (parent strain or mutant strain) was inoculated at 1% by volume into a 100-mL flask containing 10 ml of the medium for glutamic acid production shown in Table 2 below, and cultured with shaking at 200 rpm at 30° C. for 48 hours. After completion of the culturing, the concentration of L-glutamic acid in the medium was measured using HPLC (Agilent), and the results are shown in Table 3 below.

TABLE 2

| Component | Content |
|---|---|
| Glucose | 70 g/L |
| $(NH_4)_2SO_4$ | 5 g/L |
| $MgSO_4$ | 0.4 g/L |
| Urea | 2 g/L |
| Soybean hydrolyzate | 1.5% v/v |
| $KH_2PO_4$ | 1.0 g/L |
| $FeSO_4$ | 10 mg/L |
| $MnSO_4$ | 10 mg/L |
| Thiamine_HCl | 200 ug/L |
| Biotin | 2 ug/L |
| $CaCO_3$ | 5% |

TABLE 3

| Strain | L-glutamic acid production (g/L) |
|---|---|
| U3 | 10.5 |
| NMD1 | 11.41 |

As shown in Table 3 above, it was confirmed that the amount of L-glutamic acid produced by the mutant strain into which the NADP-dependent malic enzyme variant has been introduced increased by about 8.7% compared to that produced by the parent strain. These results suggest that the carbon source flux in the glutamic acid biosynthetic pathway is increased by the NADP-dependent malate enzyme variant, thereby increasing L-glutamic acid productivity.

So far, the present invention has been described with reference to the preferred embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention

[Accession Number]

Depository Authority: Korean Culture Center of Microorganisms (KCCM)

Accession Number: KCCM13218P

Deposit Date: Jun. 29, 2022

The invention claimed is:

1. A method for producing L-glutamic acid, comprising steps of:

culturing in a medium a transformant of *Corynebacterium glutamicum* U3, with an accession number KCCM13218P comprising an NADP-dependent malic enzyme variant consisting of the amino acid sequence of SEQ ID NO: 2 or a polynucleotide encoding the variant; and recovering L-glutamic acid from the transformant or the medium in which the transformant has been cultured.

* * * * *